United States Patent
Schall et al.

(10) Patent No.: US 9,247,984 B2
(45) Date of Patent: Feb. 2, 2016

(54) SUPPLY DEVICE FOR PROVIDING AN HF OUTPUT VOLTAGE, HF SURGICAL INSTRUMENT COMPRISING A CORRESPONDING SUPPLY DEVICE, AND METHOD FOR THE OPERATION OF AN HF GENERATOR UNIT

(75) Inventors: Heiko Schall, Nuertingen (DE); Martin Fritz, Tuebingen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 914 days.

(21) Appl. No.: 13/377,270

(22) PCT Filed: Jun. 9, 2010

(86) PCT No.: PCT/EP2010/003467
§ 371 (c)(1),
(2), (4) Date: Dec. 9, 2011

(87) PCT Pub. No.: WO2010/142438
PCT Pub. Date: Dec. 16, 2010

(65) Prior Publication Data
US 2012/0083781 A1  Apr. 5, 2012

(30) Foreign Application Priority Data

Jun. 10, 2009  (DE) .......................... 10 2009 024 612

(51) Int. Cl.
*A61B 5/05* (2006.01)
*A61B 18/12* (2006.01)
*A61B 18/00* (2006.01)

(52) U.S. Cl.
CPC ... *A61B 18/1206* (2013.01); *A61B 2018/00875* (2013.01)

(58) Field of Classification Search
CPC .. A61B 1/00025; A61B 1/00027; A61B 8/56; A61B 2560/0214; A61B 5/150816; A61B 5/7455; A61B 2019/2292; A61B 2018/00297
USPC .................................................. 607/27, 29, 34
See application file for complete search history.

(56) References Cited

U.S. PATENT DOCUMENTS

| 5,370,645 | A | * | 12/1994 | Klicek et al. ..................... 606/35 |
| 6,296,636 | B1 | * | 10/2001 | Cheng et al. ..................... 606/32 |
| 2004/0260281 | A1 | | 12/2004 | Baxter et al. |
| 2007/0197891 | A1 | * | 8/2007 | Shachar et al. ............... 600/374 |
| 2008/0039830 | A1 | * | 2/2008 | Munger et al. .................. 606/33 |
| 2008/0082095 | A1 | * | 4/2008 | Shores et al. ................... 606/34 |
| 2008/0091193 | A1 | | 4/2008 | Kauphusman et al. |
| 2010/0160784 | A1 | * | 6/2010 | Poland et al. ................. 600/453 |

FOREIGN PATENT DOCUMENTS

| CN | 100417365 C | 9/2008 |
| CN | 101677807 A | 3/2010 |

(Continued)

*Primary Examiner* — Theodore Stigell
*Assistant Examiner* — Natasha Patel
(74) *Attorney, Agent, or Firm* — Dickstein Shapiro LLP

(57) ABSTRACT

Supply units for providing a high-frequency RF voltage and an RF current to electrosurgical instruments so that they can be used for cutting and/or coagulating tissue, while providing regulation of the RF current and the RF voltage and providing a corresponding feedback for the treating physician. A supply unit includes an RF generator unit for generating the RF output voltage, a measuring unit for determining an electrical load while an RF output current is being applied, a signal unit for outputting a haptically perceivable (e.g., tactile) signal and a control unit that is in communicative connection at least with the measuring unit and the signal unit to activate the signal unit as a function of the electrical load.

25 Claims, 1 Drawing Sheet

(56) References Cited

FOREIGN PATENT DOCUMENTS

| DE | 44 38 978 A1 | 5/1996 |
| DE | 694 32 252 T2 | 12/2003 |
| DE | 10 2004 041 681 A1 | 2/2006 |
| DE | 601 12 714 T2 | 6/2006 |
| JP | H08-229050 A | 9/1996 |
| WO | WO 2007/092610 A2 | 8/2007 |
| WO | WO 2008/022148 A2 | 2/2008 |
| WO | WO 2009/015278 A1 | 1/2009 |

* cited by examiner

SUPPLY DEVICE FOR PROVIDING AN HF OUTPUT VOLTAGE, HF SURGICAL INSTRUMENT COMPRISING A CORRESPONDING SUPPLY DEVICE, AND METHOD FOR THE OPERATION OF AN HF GENERATOR UNIT

FIELD OF THE DISCLOSED EMBODIMENTS

The disclosed embodiments relate to a supply device for providing an RF output voltage, to an RF surgical apparatus comprising a corresponding supply device, and to a method for the operation of an RF generator unit for an electrosurgical instrument.

BACKGROUND

In radiofrequency surgery (RF surgery), a high-frequency alternate current is conducted through the human body in order to cut or coagulate tissue in a targeted manner. A general distinction is made between a monopolar application and a bipolar application of the treatment current. In a monopolar application, usually only one application electrode is provided, with a high-frequency alternate current usually being applied to the application electrode, which may, for example, be located in an electrosurgical instrument used for cutting and/or coagulating tissue. Furthermore, a large-surface neutral electrode is attached to the body of the patient. When RF current is applied, an RF voltage is applied to the application electrode and to the neutral electrode, thus closing the electric circuit across the interposed tissue. The shape of the application electrode depends on the respective field of application. The contact surface of the application electrode across which the alternate current is conducted into the tissue is relatively small, resulting in a high current density being formed in the direct environment of the application electrode and, consequently, also a great development of heat.

As the distance from the application electrode increases, the current density greatly decreases, unless there are also high current densities at other sites of the body due to considerable variations in tissue conductivity. In bipolar applications, the RF voltage is applied to two application electrodes that are located close to each other, e.g., bipolar coagulation forceps. This means that the current mainly flows through tissue located between the application electrodes. Preferably, the application electrodes are arranged on one instrument. However, often, hard to access tissue sites can only be reached and treated with difficulty, or not at all, with such instruments.

Supply devices supply the electrosurgical instruments with a suitable RF voltage and a suitable RF current, so that a problem-free treatment of the patient is possible. Desired RF current and RF voltage vary as a function of the tissue that is to be treated and also as a function of the mode of operation that is used (e.g., coagulation mode, cutting mode). Other modes of operation for different types of tissue are conceivable. Therefore, the supply device must constantly regulate the RF output voltage and/or the RF output current in order to ensure an appropriate operation of the electrosurgical instrument. Consequently, it is necessary, at times, that the operating parameters be adaptable, since the quality of the tissue that is treated with the use of an instrument changes constantly. Considering this, for example, when the conductivity of the tissue decreases, the resistance thus increases on account of the applied RF current. Conversely, untreated tissue types (e.g., fatty tissue, muscle tissue, nerve tissue) also display different resistances that must be taken into consideration in voltage or current regulation.

This regulation is desired so that the treating physician is able to safety cut and/or coagulate tissue, regardless of the type and quality of the tissue. Therefore, in order to ensure the proper functioning of the electrosurgical instrument, the supply device must control or regulate the power of the RF generator or the RF generator unit. The power that is provided in this case is usually restricted by the capacity of the generator that is being used and by the corresponding safety guidelines. Thus, it may happen that too high a power output is used without the physician noticing this. This is dangerous and can result in unwanted tissue damage. Furthermore, physicians may not be used to handling such an electrosurgical instrument because they are used to a haptic feedback (e.g., tactile feedback) when performing cutting operations.

Considering this prior art, it is the object of the disclosed embodiments to provide a supply device that allows a safe and functional operation, and facilitates the handling of an electrosurgical instrument. Furthermore, disclosed embodiments also include a corresponding RF apparatus, a method for the operation of an RF generator unit, and a method for performing an electrosurgical operation.

SUMMARY

Disclosed embodiments include a supply device for providing an RF output voltage for application by means of an electrosurgical instrument. The supply device includes an RF generator unit for generating the RF output voltage, a measuring unit for determining an electrical load while an RF output current is being applied, a signal unit for outputting a haptically perceivable signal and a control unit (including the measuring unit and the signal unit), where the control unit is disposed to activate the signal unit as a function of the electrical load.

It is a central idea of the disclosed embodiments to provide a haptically perceivable signal—in particular on the instrument—that indicates to the user the load with which the RF generator unit is being operated at the current point in time. In doing so, the surgeon or physician is provided with haptic feedback regarding various cutting parameters such as, for example, cutting speed and/or cutting depth and/or type of tissue. The signal unit and/or the measuring unit may be understood to represent logic components of the control unit that implement the specified function. The signal unit may also be a component of a regulator used for regulating the RF output voltage.

For outputting the signal, the signal unit acts on the RF generator unit in order to reduce the RF output voltage and/or the RF output current. Thus, an effect can be provided that allows, for example during a cutting operation, the voltage and/or the current on the applicator or the application electrode to drop as a function of the electrical load of the tissue. Additionally, the instrument can provide the treating physician with a sense for the applied power or the existing load. Handling of the instrument is similar to the operation of conventional mechanical instruments. The physician feels a mechanical resistance if an instrument penetrates deeply into the tissue. Accordingly, the resistance felt by the physician can be higher when a fast cut is performed by means of the electrosurgical instrument. It is possible to correlate the mechanical and the electrical resistances. For example, an activation of the signal unit can be a regulation of the RF output voltage in that, while a cutting operation is being performed in the tissue, the molecular dissolution of the tissue occurs so slowly that the movement of the instrument during the cutting operation is slowed by a noticeable mechanical contact with the tissue.

The measuring unit can include an active power calculator for calculating an active power and a control unit, in particular an adjustable resistance element, for specifying a desired value for the RF generator, this desired value being adapted to the active power. Preferably, the active power calculator is thus used to determine or estimate an active power of the applied RF current. The control unit uses corresponding measuring signals for pre-specifying the desired values for the RF generator unit. It is also possible that these desired values be control signals for controlling or regulating the operation of the RF generator unit. Consequently, the RF output voltage and/or the RF output current can be adjusted with the use of the pre-specified desired value(s).

The resistance element may have an adjustable resistance. Consequently, it is possible, for example, to vary the haptically perceivable signal over time. In doing so, the RF output voltage may drop for a short period of time when a high load occurs, so that a clear haptic feedback is achieved. As cutting is continued, the RF output voltage can again be increased in such a manner that the mechanical resistance felt by the physician is relatively low. It is also possible to compensate for the adjustable resistance of the internal resistances inherent in the supply device and for the resistances on the supply lines for the instrument. In general, the resistance element can be used for parameterizing the extent of the voltage drop of the RF output voltage. It is possible to use the resistance element for varying the mechanical resistance felt by the physician during a cutting operation and thus for varying the haptically perceivable signal.

The supply device may include an adjustment device for adjusting a desired value, in particular a desired output voltage or a desired output current or a desired output of the supply device, as well as a regulating unit for regulating the RF generator unit, consistent with the desired value. The operation of the generator unit can be controlled or regulated by means of a regulator circuit as mentioned hereinabove. In conjunction with this, voltage regulation, as well as current regulation, are conceivable. The measured load or the measured active power can be used to adapt the desired value of a corresponding regulator circuit. For example, this may be an underlying voltage regulation.

Preferably, the supply device is a supply device for operating the RF generator in a voltage-controlled mode. In a voltage-controlled mode, the RF voltage or RF output voltage delivered by the power oscillator or by the RF generator device are to be maintained at a constant value. As a cut is being performed with the instrument, the voltage of the power supply device connected to the RF generator device varies because—considering regulation technology—the device now assumes the function of a control member. In the usual voltage-controlled mode, the RF output voltage does not drop in case of a tissue impedance change. It is one intention of the disclosed embodiments to superimpose the behavior of an unregulated mode (in which the RF output voltage varies as a function of the tissue impedance) on the regulated mode (in which the RF output voltage does not generally vary) but in a controlled manner. In doing so, the characteristics of the reaction should be parameterizable and thus controllable. This object is achieved by means of an internal resistance simulation. An adjustment device for adjusting a desired value and a regulating device for regulating the RF generator unit consistent with the desired value are provided for operating the system in a voltage-regulated mode. Preferably, the supply device determines the desired value, taking into consideration the RF output current, and in particular with the use of a pre-specified value and the RF output current.

A comparator unit may be provided in order to determined the desired value. In one embodiment, the desired value is expressed by the formula $U_{Soll1}=U_0-R_i*I_a$ ($U_{Soll1}$ is a control value for the RF generator unit, $U_0$ is a pre-specified voltage value, $R_i$ is a pre-specified resistance, and $I_a$ is the RF output current). Consequently, the RF output current, and thus the tissue impedance, are considered in the determination of the desired value.

The mentioned regulating unit for the RF output voltage may include a PI (proportional-integral) regulator.

In another disclosed embodiment, an RF surgical apparatus includes a supply device (configured as described hereinabove) that further includes an internal resistance adjustment device for adjusting an internal resistance—in particular, in accordance with a supply cable resistance for the electrosurgical instrument. In conventional devices, it is not possible to adjust the internal resistance. According to the disclosed embodiments, an adjustable internal resistance is provided, and the resistance is again adjusted corresponding to the active power or the active current of the RF generator unit. Consequently, it is also possible to compensate for additional resistances, for example a cable resistance.

The RF surgical apparatus can include an electric scalpel or similar cutting instruments that are connected to the supply device.

Another disclosed embodiment includes a method for operating an RF generator unit for at least one electrosurgical instrument. The method includes regulating an RF output voltage in accordance with a control value by means of a voltage regulator, detecting an electrical load of the RF generator unit and correcting the control value as a function of the detected load.

Furthermore, another disclosed embodiment includes a method for performing an electrosurgical procedure, including the steps of setting a pre-specified value to indicate a power or voltage at which an electrosurgical instrument is to be operated, operating an RF generator unit, where the RF generator unit is operated in a voltage-controlled mode in such a manner that an RF output voltage is essentially continuously applied to the tissue in a manner consistent with a desired value, measuring an RF output current and decreasing the desired value when the measured RF output current increases in order to signal to the person performing the procedure that the impedance of the tissue is rising.

The person performing the procedure thus receives haptically perceivable feedback that makes it possible for him to estimate the existing load and/or the applied power. In the case of conventional voltage-regulated RF generator units, this is not possible.

Accordingly, the desired value can be increased when the measured RF output current increases in order to signal to the person performing the procedure that the impedance of the tissue is decreasing.

Using a cutting motion, the instrument can be guided through the tissue, and the RF generator unit is operated such that the force to be applied for the cutting motion varies as a function of the tissue impedance. Considering a regulation of the RF output current, this occurs in such a manner that this output current is slightly lower than the desired RF output current and the electrosurgical instrument is held back with a certain mechanical resistance (caused by a tissue contact with the tissue that has not yet been separated). Consequently, the cutting operation is substantially harder. On the other hand, an application of a high RF output voltage has the result that an extremely low mechanical resistance is offered so that fast and simple cutting is ensured.

Considering the mentioned methods, the result are the advantages that have already been mentioned with reference to the device. Additional advantageous embodiments are obvious from the subordinate claims.

BRIEF DESCRIPTION OF THE DRAWINGS

The disclosed embodiments will be described in greater detail, pointing out further features and advantages, by reference to the example embodiments illustrated in the drawings.

DETAILED DESCRIPTION

In the description hereinafter, the same reference numbers are used for components that are the same or for components that have the same function.

Figure 1:
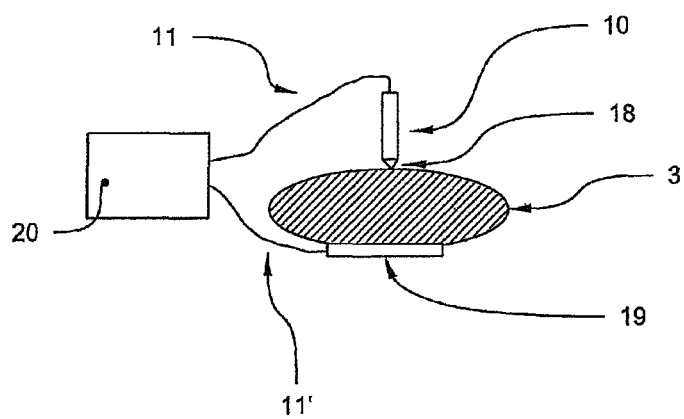
FIG. 1 illustrates a supply device connected to a monopolar instrument, in accordance with a disclosed embodiment.

FIG. 1 shows an electrosurgical apparatus including a supply device 20, a monopolar electrosurgical instrument 10 and a neutral electrode 19. The neutral electrode 19, as well as the instrument 10, are connected to the supply device 20 via a cable with appropriate lines 11, 11'. The supply device 20 includes a control unit 30 (cf. FIG. 2) that, among other things, ensures that a suitable RF output voltage $U_a$ and a suitable RF output current $I_a$ (provided by an RF generator 21) exist between the neutral electrode 19 and an application electrode 18 of the electrosurgical instrument 10. To accomplish this, the RF generator 21 and the control unit 30 are in communicative connection. The RF output voltage $U_a$ leads to a partial coagulation of the tissue of a torso 3.

Figure 2:
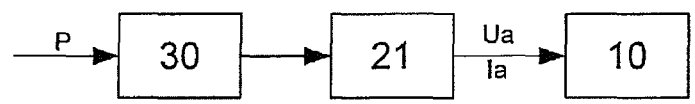
FIG. 2 is a schematic representation of a control unit of the supply device of FIG. 1, illustrating inputs and outputs.

As is clearly illustrated in FIG. 2, one aspect of the disclosed embodiments is that the control unit 30 detects an active power P of the applied RF output current $I_a$ and thus acts on the RF generator 21 in such a manner that the active power P—RF output voltage $U_a$ and RF output current $I_a$—is adjusted. The RF output voltage $U_a$ and the RF output current $I_a$ can be selected in such a manner that only a relatively low power is available for the activity to be performed with the instrument 10, e.g., the cutting of muscle tissue. As a result, the treating physician or surgeon feels a district mechanical resistance when guiding the electrosurgical instrument 10. In this manner, the electrosurgical instrument 10 is being supplied with an RF output voltage $U_a$, thus providing sufficient power for cutting, but there is a haptic feedback provided to the physician.

Figure 3:
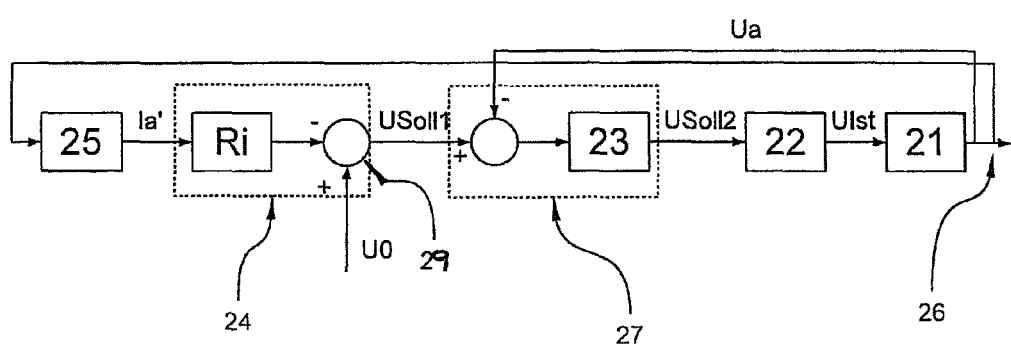
FIG. 3 is a signal flowchart for controlling or regulating the RF output voltage of the supply device in accordance with FIG. 1.

FIG. 3 shows a more detailed embodiment of the control unit 30 in accordance with the disclosed embodiments. A suitable RF output voltage $U_a$ is adjusted by voltage regulation, in which case an underlying voltage regulator 27 receives the RF output voltage $U_a$ that has been generated by the RF, generator 21 and compares this voltage with a control value $U_{Soll1}$. The difference value is input into a PI regulator 23, which then generates a desired power supply voltage $U_{Soll2}$. This desired power supply voltage $U_{Soll2}$ is input in a power supply 22 that supplies an actual power supply voltage $U_{Ist}$ to the RF generator 21, which, in turn, generates the RF output voltage $U_a$ and the RF output current $I_a$. In this way, the power made available is regulated by the RF output voltage $U_a$.

The device of FIG. 3 detects an active power P by means of an active current calculator 25. The active current calculator 25 is connected to the RF output and receives the RF output voltage $U_a$ and the RF output current $I_a$, and determines an active current $I_{a'}$. The active current $I_{a'}$ is applied to a resistor $R_i$ and the voltage drop is compared with a parameterizable RF open-circuit voltage $U_0$. The voltage drop on the resistor $R_i$ is deducted from the open-circuit voltage $U_0$ to obtain the control value $U_{Soll1}$. The resistor $R_i$ and comparator 29 thus form an $R_i$ simulator 24, which, ultimately, simulates an internal resistance of the RF generator 21. The actual internal resistance of the RF generator 21 is no longer obvious from the outside because it is compensated for by the parameterizable resistance $R_i$. The $R_i$ simulator 24 can take over the function of a signal unit for outputting a haptically perceivable signal.

The following relationship results for the control value $U_{Soll1}$ or for the desired voltage: $U_{Soll1}=U_0-R_i*I_{a'}$ where, preferably, $I_{a'}$ is the effective component of the output RF output current $I_a$. The control value $U_{Soll1}$ can be calculated by means of the comparator 29.

Analogously, it is possible to implement a current regulating system with varying internal conductance. The following relationship applies: $I_{Soll1}=I_0-G_i*U_a$ where a desired current $I_{Soll1}$ is determined by means of an adjustable pre-specified current $I_0$ of the RF output voltage $U_a$ and the parameterizable internal conductance $G_i$.

In conjunction with this, it should be pointed out that the internal resistance of the power oscillator that is present as before does not play any part and is no longer externally visible. The underlying voltage regulator levels out the internal resistance of the power oscillator.

In another application, the adjustment of a negative resistance $R_i$ is possible. The background of such a parameterizing option is the leveling-out of a cable resistance $R_{Cable}$ relative to the instrument 10 (cf., e.g., lines 11, 11') if $R_i=-R_{Cable}$. Inasmuch as the usual measurements of the RF output voltage $U_a$ and the RF output current $I_a$ always take place in or on the RF generator 21, a voltage drop across the cable with the lines 11, 11' may be ignored.

The components shown in FIG. 3 can also be understood to be a regulator circuit, where the desired value is modified with the applied load. The regulator circuit ensures a voltage-controlled operation of the supply device 20, where the RF output voltage $U_a$ (regulating parameter) is kept essentially constant or close to the control value $U_{Soll1}$. The control parameter may be the desired power supply voltage $U_{Soll2}$ or the actual power supply voltage $U_{Ist}$. Preferably, the voltage of the active power supply or the power supply 22 of the RF generator 21 varies. The regulator circuit can be implemented by the PI regulator 23 with the associate comparator. The modification of the desired value is a function of the load. This signal device is implemented by the $R_i$ simulator.

Disclosed embodiments include a supply device 20 for providing an RF output voltage for application by means of an electrosurgical instrument 10 that includes an RF generator unit 21 for generating the RF output voltage $U_a$, a measuring unit for determining an electrical load while an RF output current $I_a$ is being applied, a signal unit for outputting a haptically perceivable signal and a control unit 30 that is in communicative connection at least with the measuring unit and the signal unit in order to activate the signal unit as a function of the electrical load.

It should be noted that all the aforementioned parts are claimed as essential to the invention both alone and in any combination, particularly the details shown in the drawings. Amendments thereof are the common practice of persons skilled in the art.

The invention claimed is:

1. A supply device for providing a high-frequency RF output voltage for application by means of an electrosurgical instrument, the device comprising:
    an RF generator unit for generating the RF output voltage based on an electrical load; and
    a control unit comprising:
        a measuring unit for determining the electrical load while an RF output current of the RF generator unit is applied to the measuring unit; and
        a signal unit for outputting a haptically perceivable signal to an extent such that cutting of a tissue can be performed by the electrosurgical instrument and wherein a user of the electrosurgical instrument can feel a mechanical resistance when cutting the tissue,
        wherein the control unit activates the signal unit as a function of the electrical load determined by the measuring unit.

2. The supply device as in claim 1, wherein the signal unit outputs a signal to the RF generator unit to decrease at least one of the RF output voltage and the RF output current.

3. The supply device as in claim 1, wherein the signal unit outputs a signal to the RF generator unit to decrease each of the RF output voltage and the RF output current.

4. The supply device as in claim 1, wherein:
    the measuring unit comprises an active power calculator for calculating an active power;
    the control unit further comprises a resistance element for pre-specifying a desired voltage value for the RF generator unit; and
    the desired voltage value for the RF generator unit is based on the active power.

5. The supply device as in claim 4, wherein the resistance element comprises an adjustable resistance.

6. The supply device as in claim 4, wherein the supply device is configured in a voltage-regulated mode for operating the RF generator unit, and wherein a desired power supply voltage of a power supply device varies in order to maintain the RF output voltage essentially constant at the desired voltage value for the RF generator unit.

7. The supply device as in claim 4, further comprising:
    an adjustment device for adjusting the desired voltage value for the RF generator unit; and
    a regulator unit for regulating the RF generator unit consistent with the desired voltage value for the RF generator unit.

8. The supply device as in claim 4, wherein the desired voltage value for the RF generator unit is determined based on at least the RF output current.

9. The supply device as in claim 8, wherein the desired voltage value for the RF generator unit is calculated using a pre-specified voltage value and the RF output current.

10. The supply device as in claim 8, further comprising a comparator unit for determining the desired voltage value for the RF generator unit.

11. The supply device as in claim 10, wherein the comparator unit determines the desired voltage value for the RF generator unit in accordance with the formula: $U_{Soll1}=U_0-R_i*I_a$, where $U_{Soll1}$ is the desired voltage value for the RF generator unit, $U_0$ is the pre-specified voltage value, $R_i$ is a pre-specified resistance, and $I_a$ is the RF output current.

12. The supply device as in claim 7, wherein the regulator unit comprises a proportional-integral (PI) regulator.

13. An RF surgical apparatus comprising:
    the supply device as in claim 1; and
    an internal resistance adjustment device for adjusting an internal resistance.

14. The RF surgical apparatus as in claim 13, wherein the internal resistance adjustment device adjusts the internal resistance based on a supply cable resistance of the electrosurgical instrument.

15. The RF surgical apparatus as in claim 13, further comprising a cutting instrument connected to the supply device.

16. The RF surgical apparatus as in claim 15, wherein the cutting instrument is an electric scalpel.

17. A method for operating an RF generator unit for at least one electrosurgical instrument, the method comprising the steps of:
    regulating an RF output voltage in accordance with a control value by means of a voltage regulator;
    detecting an electrical load of the RF generator unit; and
    correcting the control value as a function of the detected electrical load,
    wherein the correcting comprises activating a haptically perceivable signal to an extent such that cutting of a tissue can be performed by the electrosurgical instrument and wherein a user of the electrosurgical instrument can feel a mechanical resistance when cutting the tissue.

18. A method as in claim 17, wherein the control value is based on a power of the RF generator unit.

19. A method as in claim 17, wherein the control value is based on an RF output voltage of the RF generator unit.

20. A method as in claim 17, wherein correcting the control value comprises decreasing the control value when there is a high detected electrical load.

21. A method as in claim 17, wherein detecting the electrical load comprises measuring an active current.

22. A method as in claim 17, wherein regulating the RF output voltage comprises calculating the control value with the formula $U_{Soll1}=U_0-R_i*I_a$, where $U_{Soll1}$ is the control value for the RF generator unit, $U_0$ is a pre-specified voltage value, $R_i$ is a pre-specified resistance, and $I_a$ is the RF output current.

23. A method for performing an electrosurgical procedure comprising the steps of:
    setting a pre-specified voltage value to indicate with what power or voltage an electrosurgical instrument is to be operated;
    operating an RF generator unit in accordance with the method as in claim 17, where the RF generator unit is operated in a voltage-controlled mode such that the RF output voltage is continuously applied to the tissue in a manner consistent with the control value;
    measuring an RF output current; and
    decreasing the control value when the measured RF output current increases in order to signal to a person performing the procedure that the impedance of the tissue is rising.

24. A method as in claim 23, further comprising increasing the control value when the measured RF output current decreases in order to signal to the person performing the procedure that the impedance of the tissue is decreasing.

25. The method as in claim 23 further comprising
    guiding the instrument through the tissue using a cutting motion; and operating the RF generator unit such that a force required for the cutting motion varies as a function of the tissue impedance.

\* \* \* \* \*